(12) United States Patent
Simmons (10) Patent No.: US 7,059,463 B2
(45) Date of Patent: Jun. 13, 2006

(54) RELEASE MECHANISM FOR ENABLING MANUAL MANIPULATION OF A MOTORIZED C-ARM

(75) Inventor: John M. Simmons, West Jordan, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/038,947

(22) Filed: Jan. 18, 2005

(65) Prior Publication Data

US 2005/0126876 A1 Jun. 16, 2005

Related U.S. Application Data

(63) Continuation of application No. 10/614,421, filed on Jul. 7, 2003, now Pat. No. 6,880,691.

(51) Int. Cl.
*H05G 1/02* (2006.01)
(52) U.S. Cl. .................... 192/95; 378/198; 474/171
(58) Field of Classification Search ............... 192/69.5
See application file for complete search history.

(56) References Cited

U.S. PATENT DOCUMENTS

| 1,438,486 | A | * | 12/1922 | Gorman | ............... | 192/93 A |
| 2,658,396 | A | * | 11/1953 | Christiance | ............... | 74/96 |
| 3,760,916 | A | * | 9/1973 | Hanks et al. | ............... | 192/69.5 |
| 3,777,643 | A | * | 12/1973 | Asbelle et al. | ............... | 396/5 |
| 4,955,046 | A | * | 9/1990 | Siczek et al. | ............... | 378/197 |
| 4,989,229 | A | * | 1/1991 | Negrelli et al. | ............... | 378/198 |
| 5,226,069 | A | * | 7/1993 | Narita | ............... | 378/197 |
| 5,583,909 | A | * | 12/1996 | Hanover | ............... | 378/197 |
| 5,619,763 | A | * | 4/1997 | Randolph et al. | ............... | 378/209 |
| 5,915,507 | A | * | 6/1999 | Maurice et al. | ............... | 188/171 |
| 6,142,667 | A | * | 11/2000 | Pattee | ............... | 378/198 |
| 6,155,713 | A | * | 12/2000 | Watanabe | ............... | 378/197 |
| 6,231,113 | B1 | * | 5/2001 | Armbruster et al. | ............... | 296/155 |
| 6,614,871 | B1 | * | 9/2003 | Kobiki et al. | ............... | 378/20 |
| 2002/0112934 | A1 | * | 8/2002 | Karambelas et al. | ............... | 192/69.43 |

FOREIGN PATENT DOCUMENTS

EP 0430338 A1 * 6/1991
WO WO 00/57785 A1 * 10/2000

* cited by examiner

*Primary Examiner*—Rodney H. Bonck
(74) *Attorney, Agent, or Firm*—McAndrews, Held & Malloy, Ltd.; Peter J. Vogel; Michael A. Dellapenna (57) ABSTRACT

A drive system for an imaging device having a curved arm. The drive system includes a carrier that engages the curved arm such that the arm can be moved along the carrier. The drive system includes a belt extending through the carrier and a motor, a drive shaft rotatably driven by the motor, and a drive pulley coupleable to the drive shaft through a clutch mechanism. The pulley engages the belt to move the curved arm relative to the carrier. The clutch mechanism is movable between an engaged position, at which the drive shaft is coupled to the drive pulley such that the motor moves the drive pulley, and a disengaged position, at which the drive shaft is uncoupled from the drive pulley so that the curved arm can be manually moved relative to the carrier. A clutch release mechanism moves the clutch between its engaged and disengaged positions.

19 Claims, 7 Drawing Sheets

RELEASE MECHANISM FOR ENABLING MANUAL MANIPULATION OF A MOTORIZED C-ARM

CROSS REFERENCE TO RELATED APPLICATIONS

This is a continuation of Ser. No. 10/614,421 filed on Jul. 7, 2003 and now U.S. Pat. No. 6,880,691.

BACKGROUND OF THE INVENTION

The present invention relates to a release mechanism for adjusting control of a drive shaft. More particularly, certain embodiments of the present invention relate to a release clutch that enables an operator to orbitally rotate a C-arm either manually or by a drive train.

Before and during a medical procedure, medical professionals may need to take several different images of a patient's body from a number of different orientations. Often it is difficult to effectively capture images from certain orientations where the imaging device is fixed and stationary. Therefore, imaging devices are mounted on large, mobile structures known as C-arm imaging machines. C-arm imaging machines typically include a mobile support structure, a carrier, and a curved, C-shaped positioning arm, or (C-arm). The carrier is mounted on the support structure and the C-arm is, in turn, slidably mounted to the carrier. An imaging source is located on one distal end of the C-arm and an imaging receiver is located on the other distal end of the C-arm. The C-arm imaging machine may be moved and rotated about a patient in a number of different orientations such that the patient is positioned between the imaging source and the imaging receiver. The C-arm imaging machine operator may then take an image of the patient.

The C-arm typically may be rotated about the patient in at least two ways. The support structure includes a rotation arm that is connected to the carrier. The C-arm has tracks along an outer periphery thereof that capture rollers on the carrier such that the C-arm is movably retained to the carrier along the rollers. A large belt extends from the carrier around the arms of the C-arm. The rotation arm may be rotated about a rotational axis such that the C-arm also rotates about the rotational axis. This is known as the rotational rotation of the C-arm. Additionally, the C-arm may be rotated along the plane of the C-arm about a transverse axis by moving the belt such that the C-arm moves, or rotates, along the carrier. This is known as orbital rotation of the C-arm. By being rotatable about at least two different axes, the C-arm may be positioned at many different orientations about a patient in order to take images from different desirable perspectives. Thus, the mobile C-arm imaging machine greatly increases the efficiency and ease of taking images of a patient before and during a medical procedure.

However, the conventional mobile C-arm imaging machine has some drawbacks. First, conventional belt-driven C-arms may only be moved manually for orbital rotation. That is to say, an operator must manually release a brake and then manipulate the C-arm to move the C-arm to a desired position. The operator then manually stops the movement of the C-arm when it reaches its desired position and activates the brake to lock the C-arm in place. While this method of adjusting the position of the C-arm may be desirable in certain situations where the operator may want to align the C-arm by hand, the manual adjustment method can be difficult and time-consuming, especially if the person performing the medical procedure must also manipulate the C-arm. Additionally, this method of adjusting the position of the C-arm may lead to imprecise positioning by the operator or any other number of problems caused by human error.

Some conventional C-arm imaging machines have a drive train that is connected to the C-arm such that an operator can use the drive train to mechanically drive the C-arm to orbitally rotate about the carrier. The operator can thus control the movement of the C-arm by operating a joystick that is electrically connected to the drive train. However, often the C-arm imaging machines that incorporate such drive trains cannot be adjusted such that the C-arm is manually manipulated. Therefore, the C-arms may not be used in emergency situations where the drive train fails or there is no power. Additionally, conventional C-arms with drive trains are large fixed-room devices that cannot be moved out of a room for use. Additionally, the drive train is in a fixed position proximate the C-arm such that it cannot be moved with the C-arm and thus may take up space and get in the way of operation of the C-arm. Additionally, there are other conventional C-arms that are mobile and incorporate a drive train, but these C-arms do not use a belt to drive the C-arm.

Therefore, a need exists for a mobile C-arm that may be manipulated either mechanically by a drive train or manually by an operator and that may be switched back and forth between such manipulation methods as necessary.

BRIEF SUMMARY OF THE INVENTION

Certain embodiments of the present invention include a drive system for an imaging device of the type having a curved arm. The drive system includes a carrier that engages and supports the curved arm such that the curved arm can be moved along the carrier. The drive system includes a belt extending through the carrier and secured about the periphery of the curved arm. The drive system includes a motor, a drive shaft rotatably driven by the motor, and a drive pulley coupleable to the drive shaft through a clutch mechanism. The pulley engages the belt such that rotation of the drive pulley effects movement of the belt and in turn movement of the curved arm relative to the carrier. The clutch mechanism is movable between an engaged position, at which the drive shaft is coupled to the drive pulley such that actuation of the motor effects movement of the drive pulley and resultant movement of the curved arm relative to the carrier, and a disengaged position, at which the drive shaft is uncoupled from the drive pulley so that the curved arm can be manually moved relative to the carrier by an operator. The drive system includes a clutch release mechanism for moving the clutch mechanism between its engaged and disengaged positions.

Certain embodiments of the present invention include a drive system having a mobile curved arm, a carrier that engages the curved arm and a belt extending through the carrier and secured about the periphery of the curved arm. The driving system is mounted to the carrier. The driving system includes a drive pulley and a drive shaft that are both engaged by a clutch mechanism. The driving system receives the belt about the drive pulley. The driving system further includes a clutch release that is movable between engaged and disengaged positions. In the engaged position, the clutch release is configured to engage the clutch mechanism such that the drive shaft is connected to the drive pulley and drives the belt in order that the curved arm moves relative to the carrier. In the disengaged position, the clutch release is configured to disengage the clutch mechanism such that the drive shaft is disconnected from the drive pulley in order that the curved arm is moved with the drive pulley moving relative to the drive shaft.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

Figure 1:
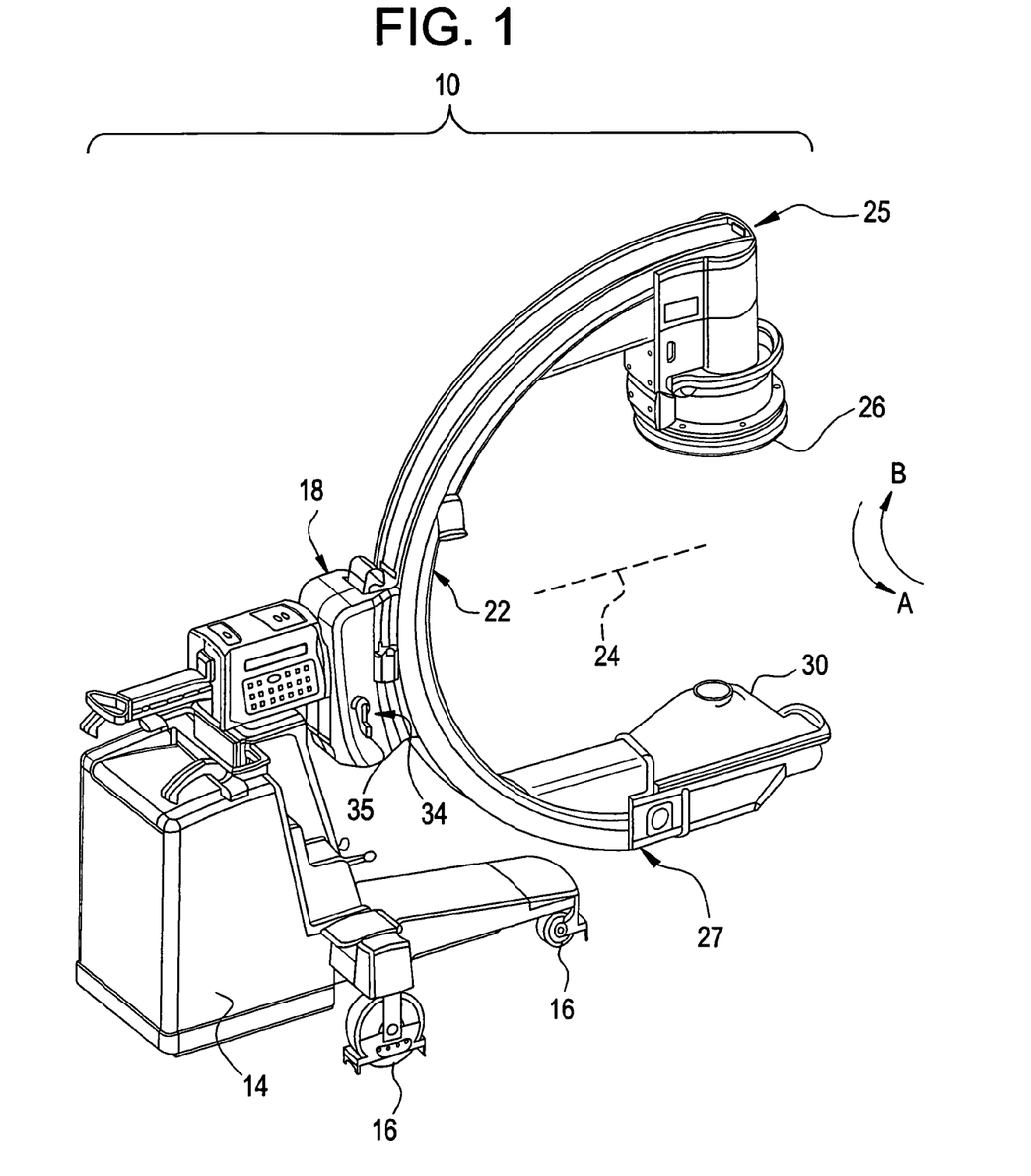
FIG. 1 is an isometric side view of a mobile imaging machine formed according to an embodiment of the present invention.

FIG. 1 is an isometric side view of a mobile imaging machine 10 formed according to an embodiment of the present invention. The imaging machine 10 includes a mobile support structure 14, a carrier 18 and a curved positioning arm 22 (which is illustrated as a C-arm). Although the curved arm 22 is illustrated as a C-arm, it will be appreciated that the arm 22 can have different shapes. For example, the arm 22 may be spiral in shape. The mobile support structure 14 has wheels 16, which allow the entire imaging machine 10 to be moved. The C-arm 22 is semicircular in shape and carries an imaging receiver 26 at a first distal end 25 and an imaging source 30 at a second distal end 27. By way of example and not limitation, the imaging source 30 may be an x-ray source. A partially covered drive system or drive train 34 is mounted to the carrier 18. A wedge-shaped clutch handle 35 extends from the covered drive train 34 and is spring loaded to remain in an engaged position.

Figure 2:
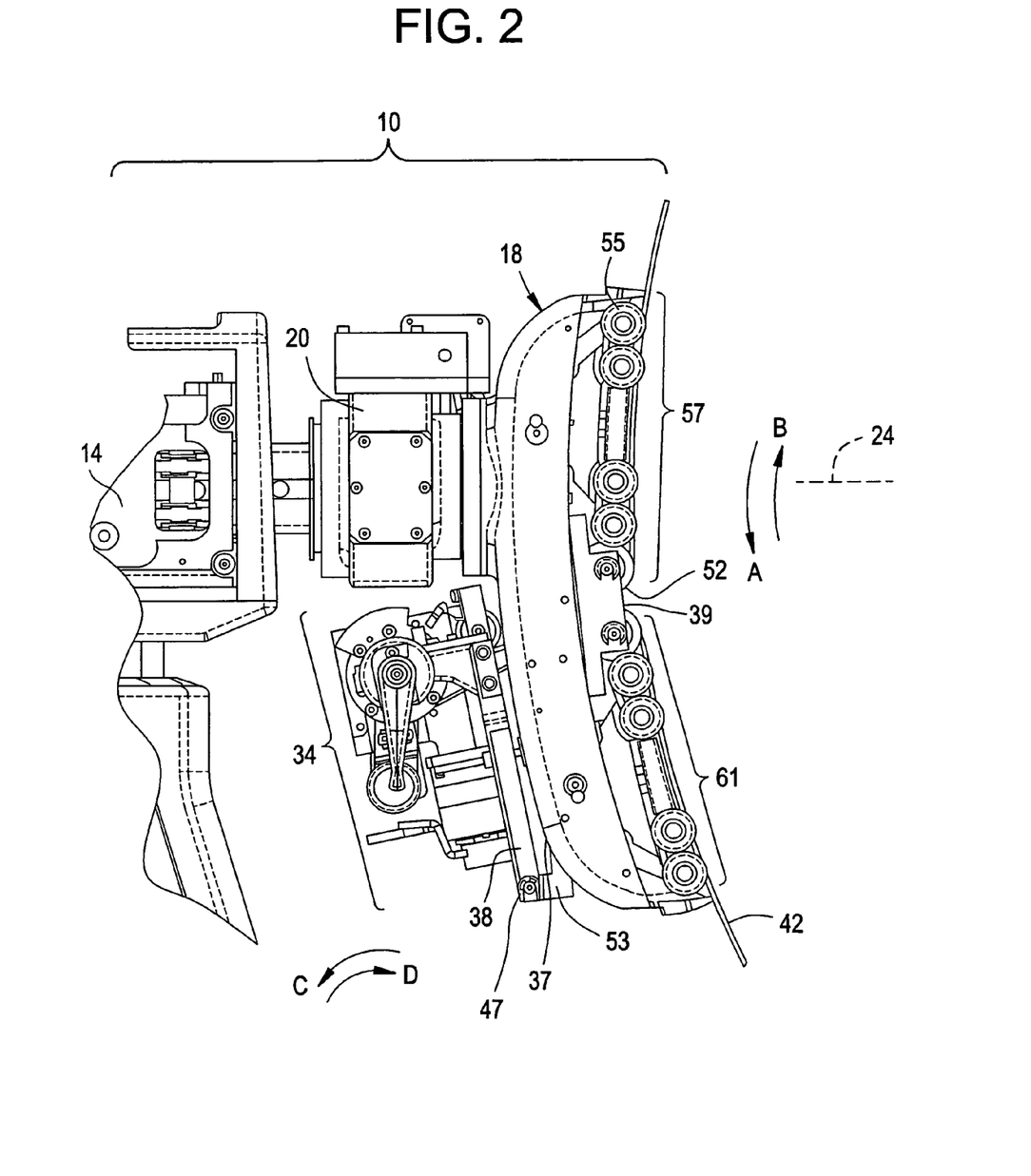
FIG. 2 is a side view of the imaging machine of FIG. 1 with a drive train exposed and the C-arm removed.

FIG. 2 is a side view of the imaging machine 10 of FIG. 1 with the drive train 34 exposed and the C-arm 22 (FIG. 1) removed. The mobile support structure 14 includes a rotational knuckle 20 that extends to the carrier 18. The rotational knuckle 20 may be manually rotated about a longitudinal axis 24 such that the entire C-arm 22 is rotated about the longitudinal axis 24. Alternatively, the rotational knuckle 20 may be driven by a motor, such as an electric motor (not shown). The motor in turn is electrically connected to a controlling device (not shown) such as a joystick to allow the operator to control the movement of the rotational knuckle 20 with the joystick.

Figure 7:
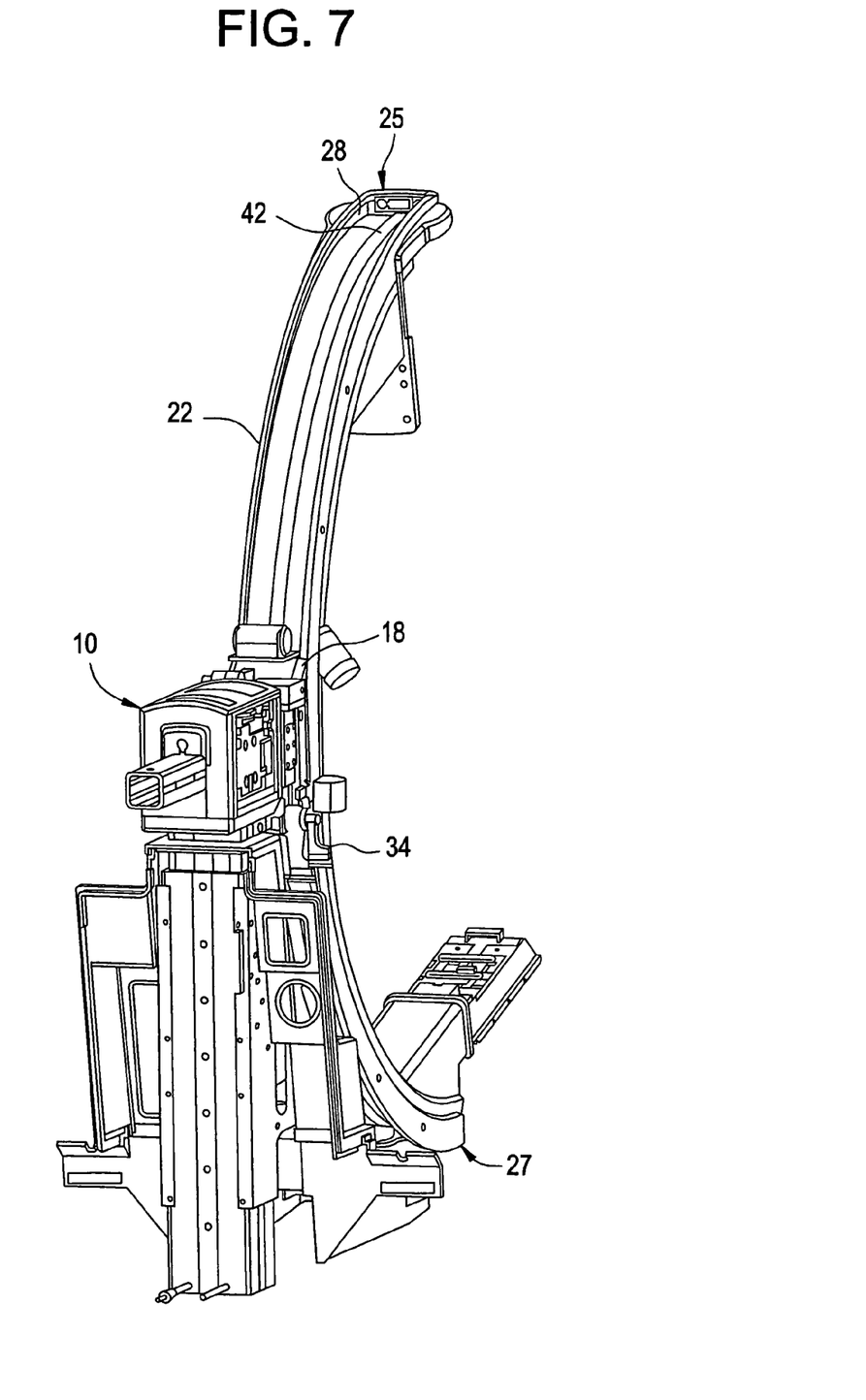
FIG. 7 is a rear isometric view of the mobile imaging machine of FIG. 1.

FIG. 7 is a rear isometric view of the mobile C-arm imaging machine 10 of FIG. 1. The C-arm 22 is movably mounted to the carrier 18. A belt 42 extends from the drive train 34 through the carrier 18, about the outer periphery of the C-arm 22 and is connected to the C-arm 22 at each distal end 25 and 27. Alternatively, the belt 42 may extend about the inner periphery of the C-arm 22. Alternatively, the belt 42 may be connected to the C-arm 22 at any number of different points besides the distal ends 25 and 27.

Returning to FIG. 1, an operator may activate the drive train 34 by pressing a button or switch connected to the drive train 34 such that the drive train 34 engages the belt 42 (FIG. 7) in order to orbitally rotate the C-arm 22 along the carrier 18 in the direction of either arrow A or B. Alternatively, the drive train 34 may be electrically connected to an electronic controlling device (not shown) such as a joystick in order that the operator can control the movement of the C-arm 22 with the joystick.

In operation, an operator may roll the mobile C-arm imaging machine 10 proximate a patient that is to be imaged. The operator positions the C-arm 22 in order that the patient is situated between the imaging source 30 and the imaging receiver 26. The operator may take an image (or series of images) of the patient and then move the C-arm 22 away from the patient. In order to position the C-arm 22 about the patient, the operator may rotate the C-arm 22 about the longitudinal axis 24 of the rotational knuckle 20 (FIG. 2) to position the C-arm 22 about the patient. Additionally, the operator may activate the drive train 34 such that the drive train 34 engages the belt 42 (FIG. 7) in order to orbitally rotate the C-arm 22 along the carrier 18 in the direction of either arrow A or B.

Manipulating the C-arm 22 by use of the drive train 34 is the default method of orbitally rotating the C-arm 22. The operator may manually override this default method by rotating the clutch handle 35 clockwise from the engaged position to a disengaged position in order to disengage the drive train 34 from the belt 42 (FIG. 7). When the clutch handle 35 is in the release position, the operator may then manually manipulate the C-arm 22 to orbitally rotate the C-arm 22 about the carrier 18. Because the clutch handle 35 is spring loaded, the operator must maintain the clutch handle 35 in the disengaged position in order to manually rotate the C-arm. When the operator has finished manually rotating the C-arm, the operator releases the clutch handle 35 from the disengaged position and the clutch handle 35 returns to the engaged position. The operator orbitally rotates the C-arm 22 in order to position the C-arm 22 about the patient such that the patient is situated between the imaging source 26 and imaging receiver 30. The operator may take an image of the patient and then move the C-arm 22 away from the patient.

In an alternative embodiment, the clutch handle 35 may not be spring loaded and may be left in either the engaged or disengaged positions. Alternatively, the clutch handle 35 may be rotated in the clockwise direction from the engaged position to the release position.

Returning to FIG. 2, the drive train 34 is mounted on a flat, substrate-shaped plate 38. Alternatively, the plate 38 may have any number of different shapes or thicknesses. The plate 38 is connected to a foot 50 extending from a backside 37 of the carrier 18 by a pin 46 such that the plate 38 can rotate about the pin 46 in the directions of arrows C and D. The belt 42 extends from the drive train 34 through the plate 38 to the carrier 18. The belt 42 extends through a hole (not shown) located midway along the carrier 18 from the backside 37 of the carrier 18 to an inner side 39 of the carrier 18 to engage the C-arm 22. The carrier 18 has an upper portion 58 on one side of the hole and a lower portion 62 on the other side of the hole. The upper and lower portions 58 and 62 each have an idler wheel 52 proximate the hole. The belt 42 extends about the idler wheels 52, and the idler wheels 52 direct the belt 42 along the carrier 18. The idler wheels 52 do not engage the C-arm 22. The upper and lower portions 58 and 62 also each have sets of rollers 54 located on the inner side 39 of the carrier 18. The belt 42 extends through the hole such that a first portion of the belt 42 extends along the upper portion 58 and a second portion of the belt 42 extends along the lower portion 62. In operation, when the C-arm 22 is connected to the belt 42, the drive train 34 activates the belt 42 such that the belt 42 can pull the C-arm 22 along the rollers 54 in the direction of either arrow A or B.

Returning to FIG. 7, the C-arm 22 has tracks 28 extending along the outer periphery thereof that capture the rollers 54 (FIG. 2) in order to retain the C-arm 22 to the carrier 18. In operation, when the C-arm 22 is connected to the belt 42 and the rollers 54, the drive train 34 activates the belt 42 such that the belt 42 can pull the C-arm 22 along the rollers 54 in the direction of either arrow A or B.

Figure 3:
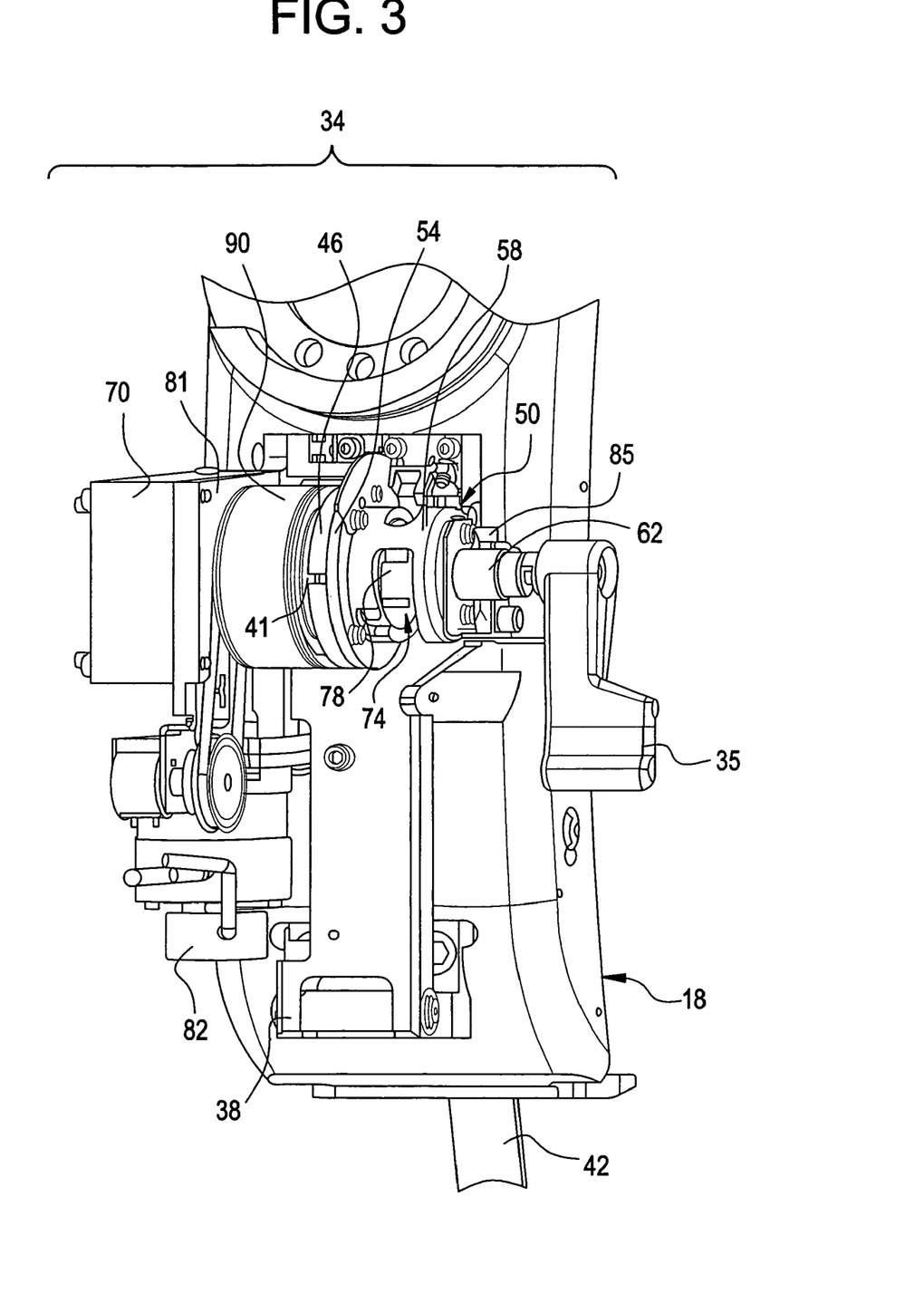
FIG. 3 is a rear isometric view of the drive train of FIG. 2.

FIG. 3 is a rear isometric view of the uncovered drive train 34 mounted on the carrier 18. The drive train 34 includes a motor 82 connected to a drive shaft 86 (FIG. 4) through a gear box 70. The gear box 70 is mounted to the plate 38 along a support wall 81. The drive shaft 86 is connected to a drive pulley 90. The drive pulley 90 drives the belt 42 to effect orbital rotation of the C-arm 22 (FIG. 1) as explained below. The clutch handle 35 can be rotated to disengage the drive pulley 90 from a drive shaft 86 (FIG. 4) to allow manual manipulation of the C-arm 22. The belt 42 is wrapped around the drive pulley 90 and extends through the plate 38 to the carrier 18. The drive pulley 90 and the belt 42 both have teeth (not shown) that engage each other in order that the belt 42 is interlocked to the drive pulley 90 and moves along with the drive pulley 90 when the drive pulley 90 rotates. The drive pulley 90 is connected to a clutch mechanism 41. The drive shaft 86 (FIG. 4) engages, and extends from, the gear box 70 through the drive pulley 90. The drive pulley 90 is mounted to the drive shaft 86 but is not interlocked with the drive shaft 86, so the drive pulley 90 rotates relative to, and independently from, the drive shaft 86. The clutch mechanism 41 engages the drive pulley 90 and the drive shaft 86.

The drive train 34 also includes a clutch release 50. The clutch release 50 includes a cylindrical middle section 58 having gaps 74 extending midway thereabout. The clutch release 50 also includes a thin cylindrical lip 54 extending around the periphery of the middle section 58 at a first end and a rod-shaped support section 62 extending from an opposite second end of the middle section 58. The drive shaft 86 (FIG. 4) extends through the clutch release 50 to the support section 62 and is retained within the clutch release 50 such that the clutch release 50 and the drive shaft 86 may rotate independently of each other. The lip 54 of the clutch release 50 is secured to securing rings 46 that extend around, and are secured to, the clutch mechanism 41. A support block 78 extends from the plate 38 and is located within the gaps 74 of the middle section 58. The clutch handle 35 is connected to the support section 62 such that as the clutch handle 35 is rotated, the entire clutch release 50, the securing rings 46, and a portion of the clutch mechanism 41 rotates with the clutch handle 35. A rectangular clutch stop 85 is connected to the support block 78 proximate the middle section 58 of the clutch release 50. The clutch stop 85 engages the clutch release 50 such that the clutch release 50 may only be rotated a desirable predetermined distance before the clutch stop 85 prevents further rotation.

Figure 4:
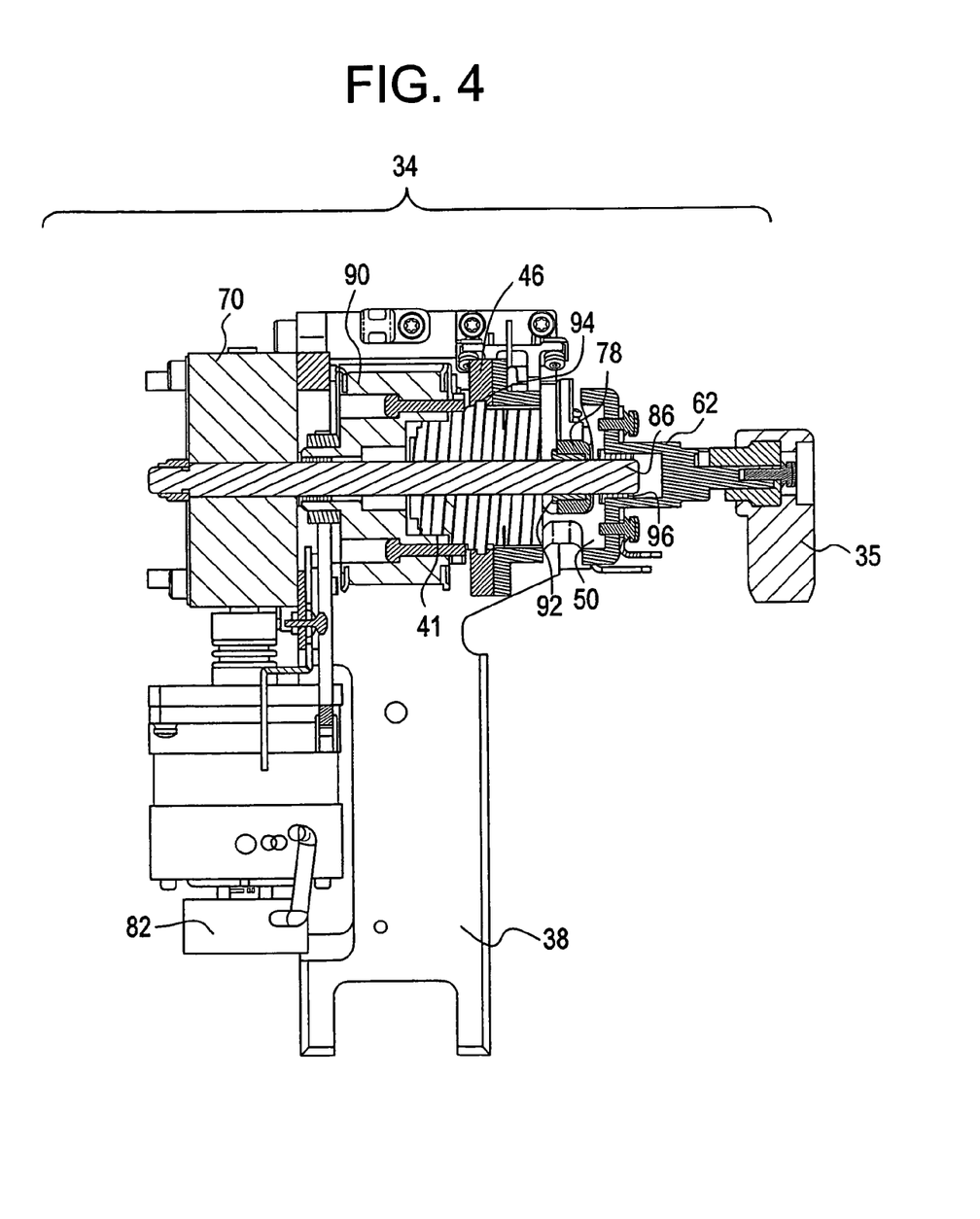
FIG. 4 is a top cutaway view of the drive train of FIG. 2.

FIG. 4 is a top cutaway view of a drive train 34 formed according to an embodiment of the present invention. A drive shaft 86 extends from the gear box 70 to the clutch release handle 35. The motor 82 is configured to drive the drive shaft 86. The drive shaft 86 engages gears within the gear box 70. The gear box 70 engages the drive shaft 86 such that the drive shaft 86 is not back-drivable, which is to say that the drive shaft 86 cannot be turned to engage the gears within the gear box 70 or the motor 82. As shown, the drive shaft 86 extends out from the gear box 70 through the drive pulley 90, the clutch mechanism 41, the support block 78, and the clutch release 50.

Figure 5:
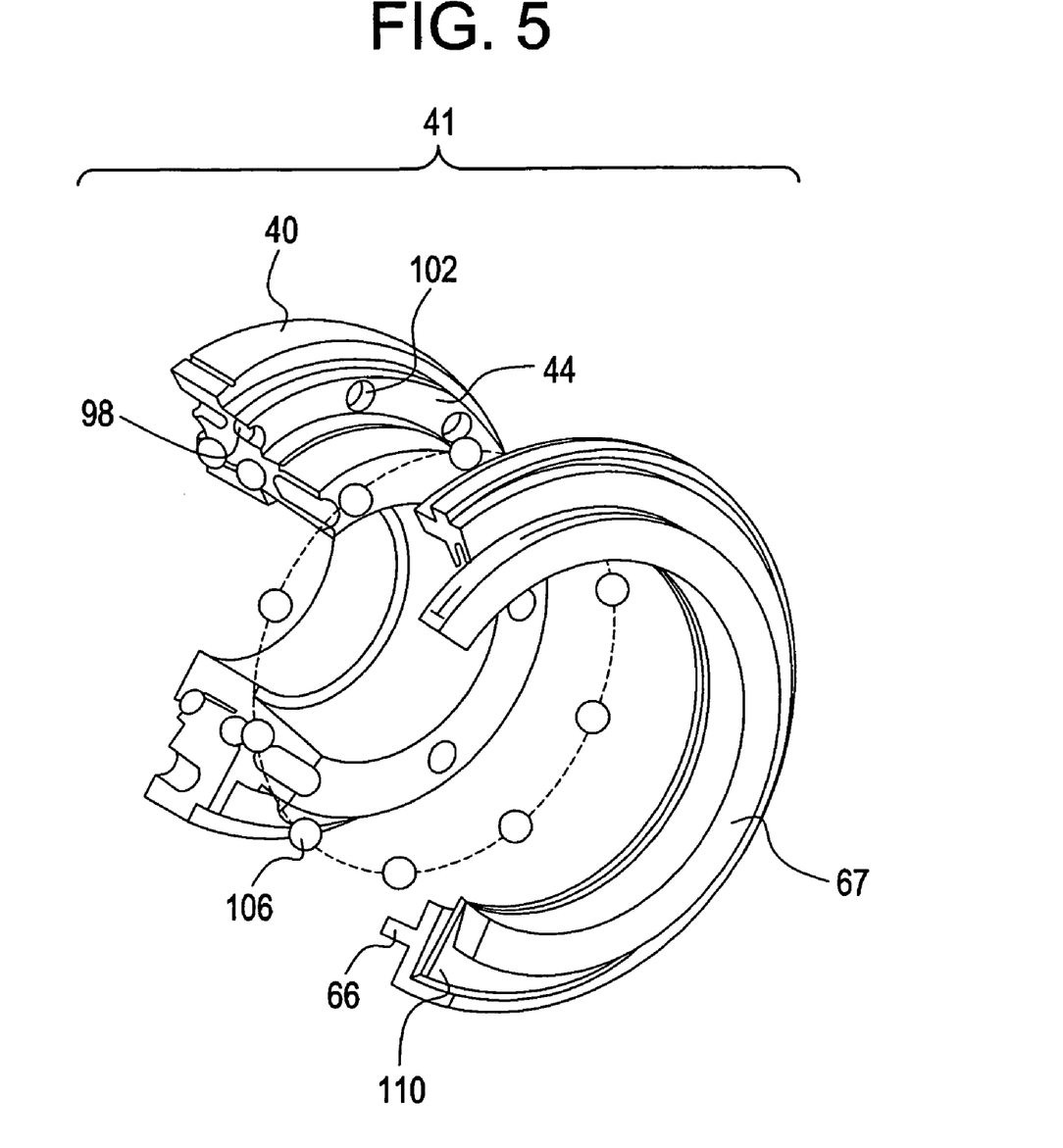
FIG. 5 is a cutaway isometric view of a clutch mechanism formed according to an embodiment of the present invention.

FIG. 5 is a cutaway isometric view of the clutch mechanism 41 formed according to an embodiment of the present invention. The clutch mechanism 41 includes first, second, and third rings 40, 44 and 66. In the drive train 34 (FIG. 3), the first clutch ring 40 is configured to be mounted to the drive pulley 90 (FIG. 3) and the second clutch ring is configured to be mounted to the drive shaft 86 (FIG. 4). The third clutch ring 66 is secured to the securing rings 46 (FIG. 3). Portions of the rings are cut away to show their internal operation. The first and second clutch rings 40 and 44 are positioned against each other. The first clutch ring 40 has circular detents 98 and the second clutch ring 44 has circular holes 102. The third clutch ring 66 has a thin, circular spring 110 aligned therealong which is held onto the third clutch ring 66 by a nut 67. When the first and second clutch rings 40 and 44 are properly positioned against each other on the drive shaft 86 (FIG. 4), the detents 98 and holes 102 are aligned. The holes 102 receive spherical balls 106. The third clutch ring 66 is mounted to the second clutch ring 44 such that the spring 110 engages the balls 106 and pushes them partially through the holes 102 into the detents 98. When the balls 106 are positioned in both the detents 98 and the holes 102, the first and second clutch rings 40 and 44 are engaged and cannot move relative to each other. Thus, since the first clutch ring 40 is connected to the drive pulley 90 and the second clutch ring 44 is connected to the drive shaft 86, the drive pulley 90 is driven by the drive shaft 86. The drive pulley 90 cannot be rotated manually when the first and second clutch rings 40 and 44 are engaged because the gear box 70 prevents the drive shaft 86 from being driven.

Since the third clutch ring 66 is connected to the clutch release 50 (FIG. 3), the clutch release 50 may be manipulated such that the third clutch ring 66 is moved away from the second clutch ring 44. The spring 110 then is pulled away from the second clutch ring 44 and the balls 106. The balls 106 are thus released from the detents 98 such that the first and second clutch rings 40 and 44 are no longer held together. The first clutch ring 40 may therefore be moved relative to the second clutch ring 44. Thus, the drive shaft 86 (FIG. 4) and the drive pulley 90 (FIG. 3) are no longer interconnected and an operator may manually move the belt 42 (FIG. 2) along the drive pulley 90 without interference from the drive shaft 86.

Returning to FIG. 4, the support block 78 extends from the plate 38 into the clutch release 50 and includes a bushing 96 that receives and supports the drive shaft 86. The drive shaft 86 may rotate within the bushing 96. Likewise, the clutch release 50 carries a bushing 96 within the support section 62 that receives and supports the drive shaft 86. The drive shaft may rotate within this bushing 96 as well. The securing rings 46 receive a lip 94 extending from the third clutch ring 66 (FIG. 5) such that the clutch release 50 is connected to the third clutch ring 66.

In operation, the motor 82 is activated, remotely by a joystick as described above, such that the motor 82 causes the drive shaft 86 to rotate. Because the second clutch ring 44 (FIG. 5) is connected to the drive shaft 86 and engages the first clutch ring 40 (FIG. 5), the drive shaft 86 in turn causes the first clutch ring 40 and the drive pulley 90 to rotate as well. The drive shaft 86 rotates within the bushings 96 in the clutch release 50 such that the clutch release 50 is not rotated. The rotating drive pulley 90 engages the belt 42 (FIG. 2) to move in the direction of the rotation of the drive pulley 90. Thus, as the belt 42 moves across the drive pulley 90 through the drive train 34, one of the distal ends 25 or 27 of the C-arm 22 (FIG. 1) is pulled toward the carrier 18 (FIG. 1) such that the C-arm 22 rotates. The drive train 34 is configured such that the drive shaft 86 may be rotated either clockwise or counter-clockwise to effect the movement of either distal end 25 or 27 of the C-arm 22 toward the carrier 18.

Figure 6:
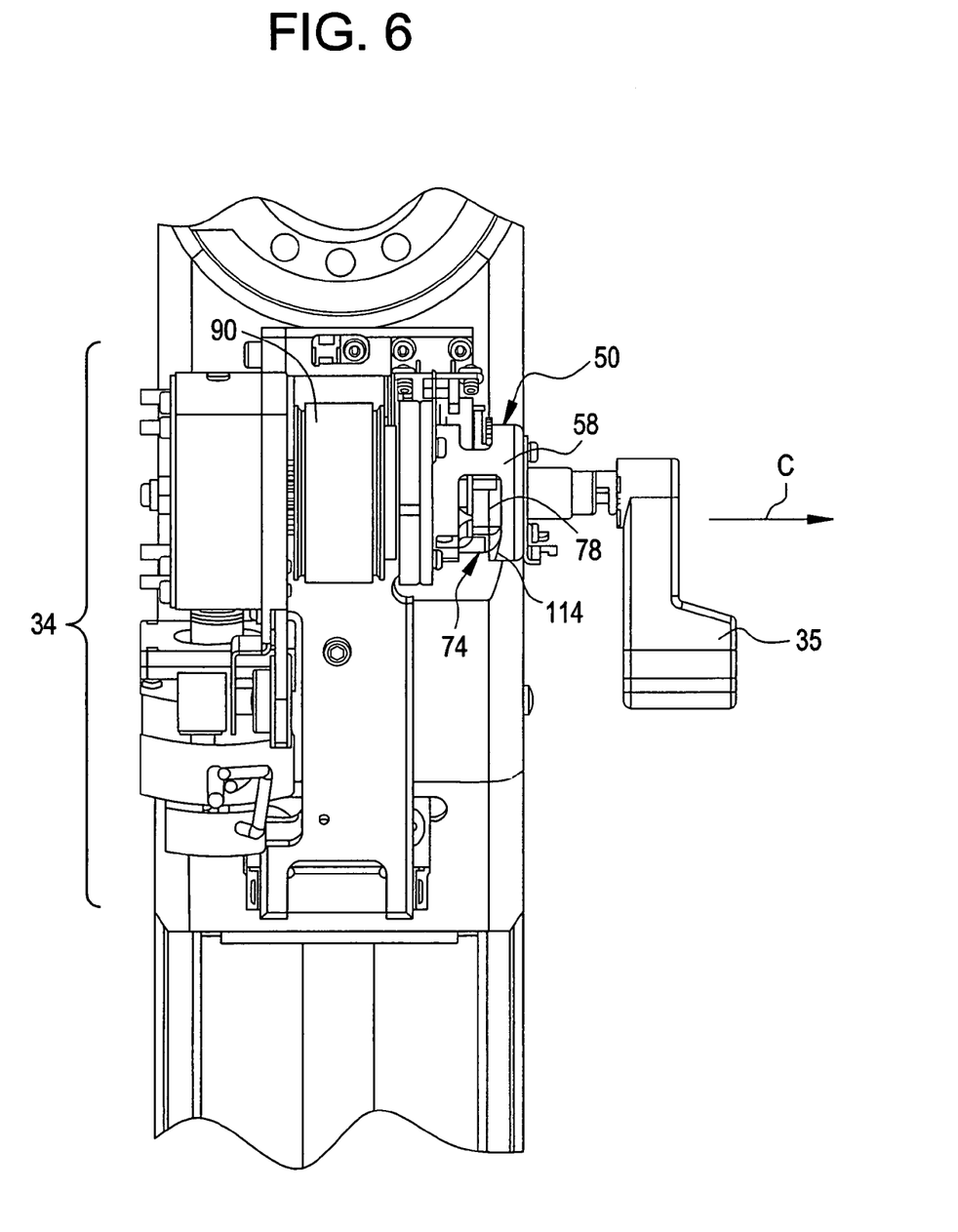
FIG. 6 is a bottom view of the drive train of FIG. 2.

FIG. 6 is a bottom view of the uncovered drive train 34. The clutch handle 35 is in the engaged position such that the first and second clutch rings 40 and 44 (FIG. 5) are engaged and held together by the spring 110 (FIG. 5) in the third clutch ring 66 (FIG. 5). A tension spring (not shown) engages the clutch release 50 in order to maintain the clutch release 50 in the engaged position. The clutch release 50 includes a ramp 114 that extends along the middle section 58 into the gap 74. Alternatively, or additionally, the clutch release 50 may have at least one other ramp 114 located on the opposite side of the middle section 58. The ramp 114 is positioned proximate the support block 78.

In operation, the operator may rotate the clutch handle 35 in the clockwise direction such that the entire clutch release 50 also rotates in the clockwise direction to overcome the resistance of the tension spring. As the clutch release 50 rotates, the ramp 114 slides along, and resistibly engages, the support block 78. Because of the orientation of the ramp 114, as the ramp 114 engages the support block 78, the entire clutch release 50 is pushed in the direction of arrow C to a release position. Since the clutch release 50 is connected to the third clutch ring 66 (FIG. 5), the third clutch ring 66 likewise is pulled in the direction of arrow C. The spring 110 (FIG. 5) on the third clutch ring 66 thus is pulled away from the second clutch ring 44 (FIG. 5) such that the first and second clutch rings 40 and 44 (FIG. 5) are disengaged from each other and free to move relative to each other. The operator may then manually move the C-arm 22 (FIG. 1) such that the drive pulley 90 rotates relative to the drive shaft 86 (FIG. 4). When the operator has manually moved the C-arm 22 to a desirable position, the operator releases the clutch handle 35. The tension spring engages the clutch release 50 such that the clutch release 50 and clutch handle 35 are rotated from the release position back to the engaged position. The first and second clutch rings 40 and 44 thus are re-engaged such that the drive pulley 90 is connected to the drive shaft 86. The drive pulley 90 and the C-arm 22 may then be driven by the drive train 34. Therefore, the clutch release 50 also operates similarly to a brake for manual operation of the C-arm 22.

The release mechanism disclosed herein may include alternative embodiments. For example, the release mechanism is not limited to use with medical imaging C-arms 22. Alternatively, the release mechanism may be used to switch operation control between the operator and the drive train in any other belt-driven machines where the belt 42 engages a curved arm. Alternatively, the drive train 34 and release mechanism may be located at other points along the carrier 18 besides at a midway point. Alternatively, the clutch release 50 may be configured such that an operator can rotate the clutch handle 35 and leave it in either the engaged or disengaged position without the clutch handle 35 being spring loaded to return to a default position. Alternatively, the clutch release 50 may be configured such that the clutch release 50 is spring loaded to remain in the release position and must be rotated to, and held in, the engaged position to operate with the drive train 34.

The release mechanism of the embodiments provides several advantages over the prior art. First, the use of the release mechanism with a drive train powered C-arm provides a mobile C-arm that has both motorized and manual orbital rotation capability. This increased flexibility of a mobile C-arm allows the operator to re-orient the C-arm more quickly than motoring the C-arm into place. It also allows an operator to move the C-arm in an emergency situation where the drive train fails or power is lost. Thus, an operator has the best of both worlds. The operator may use the drive train to move the C-arm where such precision and control is necessary but may also manually move the C-arm in situations that require adaptability.

Additionally, the release mechanism takes up very little space. Instead of being positioned on either or both distal ends of the C-arm, the drive train and release mechanism is entirely localized behind the carrier and thus out of the way of the patient, operator, or any other objects in the room. The system also saves space by positioning the drive train on the carrier instead of connecting a separate stationary drive train to the carrier. Thus, the drive train is out of the way of the operator and moves with the carrier so as not to limit or constrain the movement of the carrier. Also, the system combines a drive train with a mobile C-arm imaging machine, which greatly increases the versatility and operator control of the C-arm imaging machine.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A drive system for an imaging device of the type having a curved arm, comprising:
   a carrier that engages and supports the curved arm such that the curved arm can be moved along the carrier;
   a belt extending through said carrier and secured about the periphery of the curved arm; and
   a driving system comprising:
      a motor,
      a drive shaft rotatably driven by said motor,
      a drive pulley coupleable to said drive shaft through a clutch mechanism, wherein said clutch mechanism is manually operable, said pulley engaging said belt such that rotation of said drive pulley effects movement of said belt and in turn movement of the curved arm relative to said carrier, said clutch mechanism being movable between an engaged position, at which said drive shaft is coupled to said drive pulley such that actuation of said motor effects movement of said drive pulley and resultant movement of the curved arm relative to said carrier, and a disengaged position, at which said drive shaft is uncoupled from said drive pulley so that the curved arm can be manually moved relative to said carrier by an operator; and a clutch release mechanism for moving said clutch mechanism between its engaged and disengaged positions.

2. The drive system of claim 1, wherein said clutch release mechanism is connected to a clutch handle, said clutch handle being rotatable such that said clutch release mechanism is movable between said engaged position and said disengaged position.

3. The drive system of claim 1, further including a clutch stop that is configured to engage said clutch release mechanism in order to limit movement of said clutch release mechanism to between said engaged position and said disengaged position.

4. The drive system of claim 1, wherein said drive shaft is connected to a motor, said motor driving said drive shaft and said drive pulley when said clutch release mechanism is in said engaged position, said drive pulley being driven independently of said motor and drive shaft when said clutch release mechanism is in said disengaged position.

5. The drive system of claim 1, wherein said drive shaft is not back-drivable.

6. The drive system of claim 1, wherein said curved arm has at least one track.

7. A drive system, comprising:
a curved arm;
a carrier that engages said curved arm;
a belt extending through said carrier and secured about the periphery of said curved arm; and
a driving system mounted to said carrier, said driving system including a drive pulley and a drive shaft that are both being engaged by a clutch mechanism, wherein said clutch mechanism is manually operable, said driving system receiving said belt about said drive pulley, said driving system further including a clutch release that is movable between engaged and disengaged positions, in said engaged position, said clutch release is configured to engage said clutch mechanism such that said drive shaft is connected to said drive pulley and drives said belt in order that said curved arm moves relative to said carrier, in said disengaged position, said clutch release is configured to disengage said clutch mechanism such that said drive shaft is disconnected from said drive pulley in order that said curved arm is moved with said drive pulley and said drive pulley moves relative to said drive shaft.

8. The drive system of claim 7, wherein said clutch release is connected to a clutch handle, said clutch handle being rotatable such that said clutch release is movable between said engaged position and said disengaged position.

9. The drive system of claim 7, further including a tension spring that engages said clutch release such that said clutch release is maintained in said engaged position and automatically returns to said engaged position when said clutch release is released from said disengaged position.

10. The drive system of claim 7, further including a clutch stop that is configured to engage said clutch release in order to limit movement of said clutch release to between said disengaged position and said engaged position.

11. The drive system of claim 7, wherein said drive shaft is connected to a motor, said motor driving said drive shaft and said drive pulley when said clutch release is in said engaged position, said drive pulley being driven independently of said motor and drive shaft when said clutch release is in said disengaged position.

12. The drive system of claim 7, wherein said drive shaft is not back-drivable.

13. The drive system of claim 7, wherein said curved arm has at least one track.

14. A drive system for an imaging device of the type having a curved arm, said system comprising:
a carrier that engages and supports the curved arm such that the curved arm can be moved along the carrier; and
a drive train comprising:
a clutch mechanism, wherein said clutch mechanism is manually operable, said clutch mechanism being movable between an engaged position, at which said drive train engages said curved arm such that actuation of said drive train effects movement of said curved arm relative to said carrier, and a disengaged position, at which said drive train is unengaged from said curved arm so that the curved arm is manually moveable relative to said carrier; and
a clutch release mechanism for moving said clutch mechanism between its engaged and disengaged positions.

15. The drive system of claim 14, further including a tension spring that engages said clutch release such that said clutch release is maintained in said engaged position and automatically returns to said engaged position when said clutch release is released from said disengaged position.

16. The drive system of claim 14, wherein said clutch release mechanism is connected to a clutch handle, said clutch handle being rotatable such that said clutch release mechanism is movable between said engaged position and said disengaged position.

17. The drive system of claim 14, wherein said clutch release mechanism includes a ramp and a clutch handle, said clutch release mechanism being positioned about a support block, said clutch handle being rotatable such that said clutch release mechanism is moved from said engaged position and said ramp engages said support block such that said clutch release mechanism is moved to said disengaged position to disengage said clutch mechanism.

18. The drive system of claim 14, wherein said clutch mechanism includes first, second, and third rings, said first ring having detents, said second ring having holes with balls therein, and said third ring having a spring, said spring engaging said second ring when said clutch release mechanism is in said engagement position such that said balls extend into said detents and said holes in order that said first and second rings are connected.

19. The drive system of claim 14, wherein said clutch mechanism includes first, second, and third rings, said third ring being connected to said clutch release mechanism by a securing ring, said third ring having a spring that engages said second ring such that said second ring is connected to said first ring when said clutch release mechanism is in said engaged position, said spring being moved away from said second ring when said clutch release mechanism is moved to said release position.

* * * * *